US008329618B1

(12) United States Patent
Schafer et al.

(10) Patent No.: US 8,329,618 B1
(45) Date of Patent: Dec. 11, 2012

(54) TUBER TREATMENT COMPOSITION

(75) Inventors: Ron Schafer, Boise, ID (US); Terry Kippley, Naperville, IL (US)

(73) Assignee: Aceto Agricultural Chemical Corporation, Lake Success, NY (US)

(*) Notice: Subject to any disclaimer, the term of this patent is extended or adjusted under 35 U.S.C. 154(b) by 85 days.

(21) Appl. No.: 12/582,941

(22) Filed: Oct. 21, 2009

Related U.S. Application Data

(60) Provisional application No. 61/177,304, filed on May 12, 2009.

(51) Int. Cl.
| | |
|---|---|
| A01N 65/00 | (2009.01) |
| A01N 25/32 | (2006.01) |
| A01N 37/00 | (2006.01) |
| A23B 4/16 | (2006.01) |
| A23B 7/154 | (2006.01) |
| A23C 3/00 | (2006.01) |
| A21D 4/00 | (2006.01) |
| A23D 9/013 | (2006.01) |
| A23K 3/00 | (2006.01) |
| A23L 3/34 | (2006.01) |
| A23L 3/3463 | (2006.01) |
| C12H 1/10 | (2006.01) |

(52) U.S. Cl. ........ 504/189; 504/110; 504/142; 504/171; 504/307; 426/302; 426/312; 426/321; 426/335; 426/531; 426/532

(58) Field of Classification Search .............. 504/189, 504/110, 142, 171, 307; 426/302, 312, 321, 426/335, 531, 532
See application file for complete search history.

(56) References Cited

U.S. PATENT DOCUMENTS

| | | | |
|---|---|---|---|
| 2,708,624 A | 5/1955 | Denny | |
| 3,159,476 A | 12/1964 | Young | |
| 3,518,096 A | 6/1970 | Layton | |
| 4,857,345 A | 8/1989 | Sardo | |
| 5,436,226 A * | 7/1995 | Lulai et al. | 504/291 |
| 5,679,351 A | 10/1997 | Walter et al. | |
| 6,723,364 B1 | 4/2004 | Bompeix et al. | |
| 7,108,879 B2 | 9/2006 | Schur | |
| 7,351,420 B2 | 4/2008 | Bessette et al. | |
| 7,863,350 B2 * | 1/2011 | Brander et al. | 523/122 |
| 2005/0137090 A1 | 6/2005 | Sardo | |
| 2006/0276336 A1 | 12/2006 | Sardo | |
| 2007/0027033 A1 | 2/2007 | Sardo | |
| 2007/0078058 A1 | 4/2007 | Olson et al. | |
| 2007/0135307 A1 | 6/2007 | Olson et al. | |
| 2008/0269177 A1 | 10/2008 | Bessette | |

FOREIGN PATENT DOCUMENTS

| | | |
|---|---|---|
| CA | 539264 | 4/1957 |
| EP | 0 719 499 | 7/1996 |
| EP | 0 795 272 | 9/1997 |
| EP | 0 842 605 | 5/1998 |
| FR | 2 566 681 | 1/1986 |
| FR | 2 733 393 | 10/1996 |
| FR | 2 786 664 | 6/2000 |
| GB | 641 739 | 8/1950 |
| WO | WO 00/32053 | 6/2000 |

OTHER PUBLICATIONS http://en.wikipedia.org/wiki/Carvone; Reference materials dated Mar. 1893, 2009.*
"Non-pharmaceutical antimicrobials," Wikipedia [online] (relevant references contained here dated 2009 and 1994) [Retrieved Mar. 31, 2012] Retrieved from the Internet: <URL: http://en.wikipedia.org/wiki/Antimicrobial>.*
Gale E. Kleinkopf, et al., "Sprout Inhibition in Storage: Current Status, New Chemistries and Natural Compound," Amer J. of Potato Res (2003) 80:317-327.
U.S. Appl. No. 11/413,090, filed Apr. 28, 2006, Schafer.

* cited by examiner

*Primary Examiner* — Richard Schnizer
*Assistant Examiner* — Jane C Oswecki
(74) *Attorney, Agent, or Firm* — Oblon, Spivak, McClelland, Maier & Neustadt, L.L.P.

(57) ABSTRACT

A composition containing at least one essential oil, especially clove oil, and at least one of lactic acid ethyl ester and lactic acid n-butyl ester. A tuber having, on at least a part of a surface thereof, the disclosed composition. A method of applying the invention composition onto the surface of a tuber. A method of contacting a potato tuber "on the line" with at least one essential oil.

20 Claims, No Drawings

TUBER TREATMENT COMPOSITION

REFERENCE TO RELATED APPLICATIONS

This application claims priority to U.S. provisional application 61/177,304, filed May 12, 2009, incorporated herein by reference in its entirety.

FIELD OF THE INVENTION

The present invention relates to the use of one or more essential oils, such as clove oil, alone or in formulation, to treat tubers and/or bulbs, for example to accomplish one or more of the following: to burn back existing bud and/or sprout tissue, to inhibit sprouting of tubers, to reduce shrinkage, to maintain tuber quality and weight, to maintain firmness and turgidity, etc. The application of essential oils(s) to tubers and/or bulbs also makes up a part of the invention, especially "on the line," as do tubers and/or bulbs having essential oils(s) on at least a part of a surface thereof. Because potatoes are an important application of the present invention, they will be discussed in detail below. However, the invention is not limited thereto, and the invention includes the treatment, etc., of tubers in general such as other root crops like sweet potatoes and yams, and bulbs like onions, etc.

BACKGROUND OF THE INVENTION

It is well known in the art to treat tubers such as potatoes with various chemicals having sprout-inhibiting properties. CIPC (chlorpropham, chlorpropame; chlor-IPC IUPAC name isopropyl 3-chlorocarbanilate; isopropyl 3-chlorophenylcarbamate; Chemical Abstracts name 1-methylethyl (3-chlorophenyl)carbamate EEC no. 202-925-7) has been conventionally used for this purpose for about 40 plus years. More recently, chemicals such as various isomers of diisopropylnaphalene and other substituted naphthalenes have exhibited for their sprout-inhibiting characteristics.

Potato tubers are often treated with a chemical sprout inhibitor in the storage season, and may receive another treatment of sprout inhibitor before being packaged for shipment to retail outlets. In the absence of chemical sprout inhibitors, the ultimate storage life is greatly reduced by loss of dormancy and early sprouting. Thus, virtually all potatoes stored mid and long term are treated with chemical sprout inhibitors.

Potatoes when being dug are frequently bruised, cut and/or abraded. These injuries to the potatoes oftentimes cause spoilage during shipment, storage and the like. A process known as suberization occurs naturally which tends to heal many of these injuries. However, whenever potatoes are stored, which occurs with a particularly large portion of potatoes harvested in any given year, if healing occurs slowly, a significant loss of potatoes can occur through spoilage. Early treatment with certain sprout inhibitors, such as CIPC, may retard the suberization process, thus contributing to the loss of potatoes through spoilage.

The main sprout inhibitors registered for use on potatoes are (CIPC), maleic hydrazide (MH), and dimethylnaphthalene (DMN) and Diisopropylnaphthalene (DIPN). The two chemicals in combination (CIPC plus DIPN) appear to be more effective at lower concentrations than either of the two chemicals alone. Simultaneous application of CIPC and DIPN provides improved results over application of either sprout inhibitors separately.

For example, it is relatively common in the potato storage industry to treat potatoes with Chloroisopropyl-N-carbamate (CIPC) to prevent or retard development of sprouts in the potatoes. Even though untreated potatoes are stored at a cool temperature, for example, generally between about 36-52° F., sprouting does begin to occur after a month or more of storage. Storage of upwards of six to ten months is typical for stored potatos. Thus, without treatment of a chemical such as CIPC, the stored potatoes become entangled in sprouts and the whole stored lot of potatoes may become economically useless. Although early treatment with CIPC could be advantageous for sprout inhibition purposes, application of CIPC is typically delayed until after suberization has occurred inasmuch as CIPC tends to retard suberization, resulting in accelerated rot and spoilage.

CIPC is typically applied in one or multiple applications to the tubers to be stored using thermal fogging techniques, sprays and powders. Conventional thermal fogging involving the application of CIPC into a stream of hot air or onto a hot surface of 500-1000 ° F., to produce a CIPC aerosol. The CIPC aerosol is circulated through potatoes piled in a potato storage building with the use of fans. Preferably the potatoes are turgid rather than soft when treated with the CIPC aerosol, since a pile of softened potatoes may be substantially compressed thereby impeding distribution of the aerosol. CIPC residue levels, will, however, typically decrease over time due to biodegration, venting and atmospheric loss. To extend the effective sprout inhibiting capability of CIPC, further applications may be needed.

CIPC is used in significant quantities world wide and is capable of suppressing sprouts on stored tubers with the chemical ability to limit cell division. Increased rates, multiple applications, addition of substituted naphthalene chemistries coupled with strict storage management strategies have been implemented to help reduce sprout development in CIPC treated potatoes. Yet the tubers often develop swollen white bud tissue and small peeping sprouts that are undesirable and when present can reduce the fresh pack potato value from 50% to 100% (complete rejection) at the point of delivery. The instant invention provides, among other things, an effective treatment protocol that darkens and/or burns back these unwanted buds and small sprouts and allows the potatoes to be wholly valued in the market and compliments the use of CIPC. It also provides assurance of less shrink (weight loss) and maintains the tuber quality over and above the use of CIPC EC alone.

DETAILED DESCRIPTION OF THE PREFERRED EMBODIMENTS

The present invention relates to an essential oil formulation and to the use of essential oil(s) alone or in formulation, including use "on the line." The invention essential oil formulation may be combined with one or more sprout inhibitors, such as CIPC and others. The application of essential oil(s) to tubers and/or bulbs also makes up a part of the invention, both alone and in any combination (physical, sequential, etc.), as do tubers and/or bulbs having one or more essential oils or an essential oil formulation on at least a part of a surface thereof. The tubers and/or bulbs treated according to the invention may be in any stage of their "lifecycle" (natural and commercial) when the invention essential oil or essential oil formulation is applied thereto.

Any essential oil can be used herein, including for example any one or more of the following essential oils:

| | | |
|---|---|---|
| Allspice | Elemi | Patchouli |
| Angelica | Eucalyptus | Pennyroyal |
| Aniseed | Fennel | Peppermint |
| Basil | Frankincense | Petitgrain |
| Bay | Geranium | Pimento |
| Benzoin | Ginger | Pine |
| Bergamot | Grapefruit | Rose |
| Birch | Helicrysum | Rosemary |
| Bitter almond | Hyssop | Rosewood |
| Black pepper | Jasmine | Rue |
| Boldo | Juniper | Sage |
| Buchu | Lavandin | Sandalwood |
| Cajuput | Lavender | Spearmint |
| Calamus | Lemon | Spikenard |
| Camomile | Lemongrass | Tagetes |
| Camphor | Lemon verbena | Tangerine |
| Cardamom | Lime | Tansy |
| Caraway | Mandarin | Tarragon |
| Carrot seed | Marjoram | Tea tree |
| Cassia | Melissa | Thuja |
| Cedarwood | Mugwort | Thyme |
| Cinnamom | Mustard | Vanilla |
| Citronella | Myrrh | Vetiver |
| Clary saga | Neroli | Wintergreen |
| Clove | Niaouli | Wormwood |
| Coriander | Nutmeg | Yarrow |
| Cumin | Orange | Ylang-ylang |
| Cypress | Oregano | |
| Dill | Palma rosa | |

A preferred essential oil herein is one comprising eugenol ($C_{10}H_{12}O_2$), found for example in clove oil:

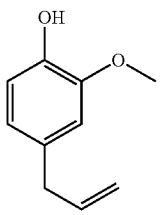

In addition, neat eugenol can be used in the invention in place of, or in addition to, any essential oil, including those essential oils containing eugenol.

Peppermint oil, spearmint oil and especially clove oil are preferred herein.

In the invention essential oil formulation at least one essential oil is formulated with (i.e., physically present together with) at least one of lactic acid ethyl ester (ethyl lactate) and lactic acid n-butyl ester (butyl lactate):

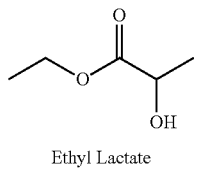
Ethyl Lactate
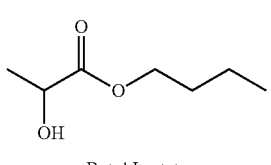
Butyl Lactate

In addition, other butyl lactate esters can be used in addition to or in replacement of n- butyl lactate.

The invention essential oil formulation preferably forms a mixture that is wholly compatible with commercially available sprout inhibitors used for sprout suppression in fresh pack potatoes. This unique combination allows for the application of essential oils(s) (e.g., clove oil) directly to the potatoes in a fresh pack operation. This combination preferably delivers the active ingredient of essential oils(s) to burn back existing bud and sprout tissue and a sprout inhibitor which suppresses new bud and sprout tissue from emerging.

As used therein, the term "fresh pack" means potatoes being washed sorted and packaged, for example to be sold fresh (uncooked), for example for sale and distribution to restaurants and consumers.

As used herein, the term "on the line" means directly injected into a supply line for application of the essential oil or essential oil formulation onto, e.g., fresh pack potatoes, or batched mixed in a tank supplying a nozzle-based application onto, e.g., fresh pack potatoes. The application is preferably made to washed potatoes (tubers) passing over a rolling table equipped with rollers, rolling brushes, sponge rollers, etc. The application can also be accomplished with a drench treatment, dip treatment or flume treatment, or by sprinkling, spraying or immersion.

Sprout inhibitors useful herein include CIPC (chlorpropham, chlorprophame; chlor-IPC IUPAC name isopropyl 3-chlorocarbanilate; isopropyl 3-chlorophenylcarbamate; Chemical Abstracts name 1-methylethyl (3-chlorophenyl) carbamate EEC no. 202-925-7), diisopropylnaphalene, other substituted naphthalenes, and those described in U.S. patent publications 2007/0135307 and 2007/0078058, both incorporated herein by reference. Commercial sprout inhibitors useful herein include Shield, Shield 3 EC and Sprout Nip 2 EC. The combination of the invention essential oil formulation with one or more sprout inhibitors help keep the potato sprouts inhibited throughout the marketing process to the end consumer. This is a marked improvement over common fresh pack operations.

The present essential oil formulation preferably comprises 1, 5, 10, 20, 30, 40, 50, 60, 70, 80, 90, 99, etc. %, based on total weight, including all values and subranges between stated values, of one or more essential oils, preferably more than 20%, more preferably more than 30%, even more preferably more than 40% of essential oil. Preferably, less than 90% is present, more preferably less than 75% is present. In a preferred embodiment 45, 50, 55, 60, 65, or 70% of one or more essential oils is present.

The present essential oil formulation preferably comprises 1, 5, 10, 20, 30, 40, 50, 60, 70, 80, 90, 99 etc. %, based on total weight, including all values and subranges between stated values, of at least one of ethyl lactate and butyl lactate, preferably more than 20%, more preferably more than 30%, even more preferably more than 40% of at least one of ethyl lactate and butyl lactate. Preferably, less than 90% is present, more preferably less than 75% is present. In a preferred embodiment the total amount of ethyl lactate, butyl lactate, and any emulsifiers present is less than 60%, including 58, 55, 50, 45, etc.% and less.

When the present essential oil formulation comprises sprout inhibitor, it preferably comprises 1, 5, 10, 20, 30, 40, 50, 60, 70, 80, 90, 99 etc. %, based on total weight, including all values and subranges between stated values, of sprout inhibitor, preferably more than 10%, more preferably more than 15%, even more preferably more than 20% of sprout inhibitor. Preferably, less than 90% is present.

An optional ingredient in the present essential oil formulation is lactic acid itself.

Other optional ingredients may be present in the invention formulation. These include diluents such as water, other solvents (e.g., ethanol, etc) and surfactants. Combinations can be used. Any, any combination, or all of nonionic, anionic, zwiterionic, nonionic, and cationic surfactants can be used. An example is Stepan AGENT 2995-3. Stepan AGENT 2995-3 is a specially formulated blend of anionic, nonionic surfactants, and solvent specifically designed for use in Aceto's CIPC 3E formulation. Stepan AGENT 2995-3 was developed to be used at 63% as a post-harvest emulsifier. The amount of surfactant is not limited and can be from 0.01 -40% of the total weight of the invention formulation, as an example. The amount of diluent is not limited and can be from 0.01 -90%+ of the total weight of the invention formulation, as an example.

Stepan AGENT 2995-3 has the following typical properties:

Appearance @ 25° C. Clear, Amber Liquid
Specific Gravity @ 25° C. 0.91
Density @ 25° C., lbs/gal 7.6
Moisture, % 0.1
pH, 5% in 50:50 IPA:H20 5.7
Viscosity @ 25° C., cps 18
Pour Point, ° F. 24
Flash Point, PMCC, ° F. >201
DOT Classification Non-Hazardous A typical invention essential oil formulation contains the following ingredients in the following amounts (W/W):

| clove oil | CAS 8015-97-2 | 50% |
| ethyl lactate | CAS 97-64-3 | 50% |

The present invention essential oil formulation can be added to a spray tank and mixed, or directly injected and mixed into the spray supply line or batch mixed in a holding tank One example of how such an essential oil formulation may be used is as follows:

3.92% (e.g., 1.36 gallons essential oil formulation per 34.64 gallons water) to 17.36% (e.g., 5.48 gallons essential oil formulation per 30.52 gallons water) essential oil formulation in water solution is applied at a rate of 1 quart per ton of potatoes. The end result is to apply from 40 ppm of essential oil formulation (20 ppm A.I. clove oil) to 159.2 ppm of formulation (79.6 ppm A.I. clove oil) per pound (454.4 grams) of potato.

Another typical invention essential oil formulation contains the following ingredients in the following amounts:

| clove oil | CAS 8015-97-2 | 60% |
| ethyl lactate | CAS 97-64-3 | 40% |

The amount of invention essential oil and invention essential oil formulation applied to a tuber or bulb is not limited and can range, for example, from 0.000001 -1 g per tuber or bulb and more including all values and subranges between stated values.

As used herein, the term "tuber" is inclusive of "potato tuber." "Potato tuber" refers to the underground storage organ of the potato plant (Solanum tuberosum). The potato tuber is a modified stem and includes buds that can sprout and form new potato plants. The term "(potato) tubers" refers to both tubers generally and to potato tubers. Preferred potatoes include Russet Burbank, Ranger Russet, Umatilla Russet, Shepody, Norkotah Russet, Yukon Gold, Norchip, Gem Russet, Atlantic, Chipeta, Snowden, and Dark Red Norland.

The phrase "effective to inhibit sprouting" means that: (a) the number, and/or the weight, of buds and sprouts/stems (sprouts) growing from a defined number of (potato) tubers contacted with a composition in accordance with the present invention (e.g., at least one essential oil or at least one essential oil formulation) is less than the number, and/or the weight, of sprouts growing from the same number of control (potato) tubers (of the same cultivar as the treated (potato) tubers) that were not contacted with a composition in accordance with the present invention; and/or (b) the average rate of growth of buds, stems growing from a defined number of (potato) tubers contacted with a composition in accordance with the present invention is less than the average rate of growth of buds, stems growing from the same number of control (potato) tubers (of the same cultivar as the treated (potato) tubers) that were not contacted with the composition. Such inhibition can be at any time as compared to the control. As understood by those in this field, the concept of inhibition is meaningful when control tubers show activity being inhibited in tubers contacted with at least one essential oil or at least one essential oil formulation in accordance with the invention. Another preferred measure of inhibition is a comparison between the total amount of "dormant or darkened bud or sprout tissue or bud or sprout tissue burned back compared to white healthy bud or sprout tissue, e.g. 24 hours after treatment up 4 weeks after treatment compared to untreated control. Whichever measure is used, preferred amounts of inhibition include less than 1%, 1%, 3%, greater than 3%, 5%, 8%, 10%, 20%, 30%, etc. to 100%.

The essential oils(s) and other ingredients used herein can be purchased commercially, or synthesized or obtained based on existing literature. They (i.e., the essential oils described herein and the invention essential oil formulations described herein) can be used alone or in mixture, and can be applied together with other materials such as other sprout inhibitors. By "together," we mean that they can be used in mixture with other materials such as active agents upon application to, e.g., potatoes, and/or can be used sequentially before, during, and/ or after application of any other material.

In general, the present invention includes any application of essential oils(s) and/or the invention essential oil formulation to tubers and or bulbs, and particularly includes application to potato plants in the field before the potatoes are harvested, and/or application after the potatoes are harvested but before they are stored, and/or application after the potatoes are in storage, and/or "on the line." In another preferred embodiment the essential oil(s) or invention essential oil formulation is applied via an aerosol, spray or thermal fog, to harvested potatoes. Methods of application also include via aerosol can and via smoke generators, for example for treatment in rail cars. Essential oil(s) may also be first or subsequently applied after tubers (potatoes) have been harvested and stored for a sufficient period that bruises and cuts have healed, i.e., suberization has occurred. In another aspect of the invention, the essential oil(s) is applied such that it inhibits sprouting during the potato shipping and distribution process and/or to burn back existing bud and/or sprout tissue and/or to inhibit sprouting of tubers.

In accordance with the foregoing, and in one embodiment, the present invention preferably provides methods for inhibiting sprouting during the potato shipping and distribution process and/or to burn back existing bud and/or sprout tissue and/or to inhibit sprouting of tubers, and maintain quality reducing shrink, the methods each including the step of contacting a potato tuber or a bulb with an amount of at least one essential oil, wherein the amount of the at least one essential oil is effective to inhibit sprouting during the potato shipping and distribution process and/or to burn back existing bud and/or sprout tissue and/or to inhibit sprouting of tubers.

Typically, the at least one essential oil is applied simultaneously, or substantially simultaneously, to numerous, harvested, potato tubers. In the practice of the methods of the invention the at least one essential oil is typically applied after the potato tubers have been harvested, but typically not later than the onset of sprouting. In some embodiments of the methods of the invention, the effective amount of the at least one essential oil is that amount sufficient to provide a dosage of from far less than 1 mg essential oil per/1 kg (potato) tubers (e.g., 1 parts per million (ppm)) to, e.g., 100 ppm and above.

In a preferred embodiment of the invention, the at least one essential oil, whether alone or in formulation, is applied after the potato tubers have been harvested, but typically not later than the onset of sprouting. Thus, in some embodiments of the methods of the invention, the at least one essential oil or essential oil formulation is applied to the tubers within one, two, three, four five, six, seven or eight weeks after the tubers are harvested. Typically, the at least one essential oil or essential oil formulation is applied before the end of the natural dormancy period of the harvested potato tubers, i.e., before the buds on the potato tubers have begun to sprout. In one embodiment the at least one essential oil is applied as close to the end of the natural dormancy period as is practical. The duration of the natural dormancy period is known to those of skill in the art and varies between potato cultivars, and depends on such factors as the physiology and condition of the tubers at harvest, and the storage temperature. For example, depending on temperature and potato cultivar estimates (in days) of the natural dormancy period falls between about 70-140 days at temperatures of 45 -48° F.

If potatoes are subject to reconditioning, the at least one essential oil or essential oil formulation is typically applied at the beginning of the reconditioning period. Thus, in some embodiments of the invention, the at least one essential oil or essential oil formulation is applied one, two, three, four or five weeks before potato tubers are processed to make french fries or potato chips. In the practice of the methods of the invention, the at least one essential oil or essential oil formulation may be applied to the potato tubers on more than one occasion (e.g., at least twice) during the storage period.

In one embodiment, but not as a requirement, the at least one essential oil or essential oil formulation is applied simultaneously, or substantially simultaneously, to numerous, harvested, potato tubers stored in bulk storage sheds designed to hold anywhere from, e.g., 5000 to 25000 tons. The sheds are designed to precisely control ventilation through the bulk pile (which may be about twenty five feet deep) along with temperature and relative humidity. Temperature is controlled by refrigeration and/or ventilation with outside air through cell decks which also raises the humidity. For example, the at least one essential oil or essential oil formulation can be volatilized at high temperature and applied as a thermal fog into the storage ventilation system that circulates air through the potato pile, from bottom to top. The storage sheds are generally closed tight after fogging, and the air may be circulated internally through the pile for several hours after application of the at least one essential oil or essential oil formulation. Again by way of example, the at least one essential oil or essential oil formulation can also be atomized or vaporized with various types of nozzles (e.g., air assisted, ultra-sonic or pressurized aerosol cans) or humidification apparatus to include centrifugal or cell decks and introduced onto the surface of one or more tubers via, e,g, the ventilation system of a storage sheds, or transit containers via humidification-type apparatuses such as humidifiers, drums, evaporators, filter pads, centripetal devices, and air assistance sprayers and via aerosol cans (smoke generators). Drenches, dips, dusts and sprays can also be used to apply the at least one essential oil or essential oil formulation. The at least one essential oil or essential oil formulation can also be impregnated on filters, or other inert materials, to facilitate slow release over time through the ventilation system of the storage sheds. The at least one essential oil or essential oil formulation can also be applied as an emulsifiable concentrate for spraying onto fresh market potatoes as they go through sorting and packing lines prior to bagging.

The methods of the present invention are applicable to any potato cultivar including, but not limited to, Russet Burbank, Ranger Russet, Umatilla Russet, Shepody, Norkotah Russet, Yukon Gold, Norchip, Gem Russet, Atlantic, Chipeta, Snowden, and Dark Red Norland.

EXAMPLES

Treatments:
SHIELD EC™ alone and SHIELD EC™+FRESH PACK 50 EC™

SHIELD EC™ contains the following ingredients in the following amounts based on total weight: 36.73% CIPC Technical plus 63.27% Stepan Agent 2995-3.

FRESH PACK 50 EC™ contains the following ingredients in the following amounts based on total weight: clove oil 50%, Lactic acid, ethyl ester 50%, 4.33 pounds A.I. per gallon.

Trial #1

Materials and methods.

A fruit Pressure Tester Model FT 327 from QA Supplies LLC Norfolk Va. was used in this testing.

A one inch square was cut from the center of each tuber running the entire length, providing a one inch square center cut french fry. The large fry was suspended across the press table supported on each end by a ¼ inch square rod spaced 4 inches apart. Using a 11.25 mm tip on the Pressure Tester mounted in a manual press, pressure was applied to the center of the 4 inch span until the fry bent enough to touch the table of the press. The 11.25 mm tip applied pressure but did not penetrate the potato. The amount of force required to bend the fry ¼ inch was recorded in Kg.

New fresh potatoes were used for comparison.

| Results | |
| --- | --- |
| Shield | Force Kg |
| 1 | 1.5 |
| 2 | 1.1 |
| 3 | 2.2 |
| 4 | 1.2 |
| 5 | 1.6 |
| Total | 7.6 |
| Average | 1.52 |
| Shield + Fresh Pack EC 50 | Force Kg |
| 1 | 3.7 |
| 2 | 3.8 |
| 3 | 2.6 |
| 4 | 4.35 |
| 5 | 4.6 |
| Total | 19.05 |
| Average | 3.81 |

-continued

| Results | |
| --- | --- |
| Fresh Store Purchased Tubers | Force Kg |
| 1 | 5.6 |
| 2 | 5.0 |
| 3 | 6.75 |
| 4 | 5.9 |
| 5 | 6.25 |
| Total | 29.5 |
| Average | 5.9 |

The Fresh Pack + Shield treated tubers are more turgid (rigid) and firmer than the tubers treated with Shield alone. The Fresh Pack + Shield treated tuber compare more closely to the newly purchased potatoes than to the tubers treated with Shield alone.

The present invention essential oil and essential oil formulation can also be used in any way described for the treatment composition disclosed in U.S. 2007/0027033. In addition, the essential oil formulation of the present invention can contain, in addition to or in place of, the invention essential oil any of the active principles described in U.S. 2007/0027033 such as a salt of eugenol fit for human consumption, isoeugenol, a salt of isoeugenol fit for human consumption, etc. U.S. 2007/0027033 is incorporated herein by reference in its entirety. In this regard, a preferred method herein is an anti-germination method for bulbs and tubers including the application to said bulbs or tubers of the present invention essential oil or essential oil formulation, said method including the application by sprinkling, spraying or immersion at, above or below ambient temperature of said invention essential oil or essential oil formulation on the bulbs and tubers after storage.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out. Terms such as "contain(s)" and the like as used herein are open terms meaning 'including at least' unless otherwise specifically noted.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

What is claimed is:

1. A composition comprising:
   at least one essential oil,
   at least one of lactic acid ethyl ester and lactic acid n-butyl ester, and
   at least one sprout inhibitor.

2. The composition according to claim 1, comprising clove oil.

3. The composition according to claim 1, comprising lactic acid ethyl ester.

4. The composition according to claim 1, comprising lactic acid n-butyl ester.

5. The composition according to claim 3, comprising clove oil.

6. The composition according to claim 4, comprising clove oil.

7. A tuber comprising, on at least a part of a surface thereof:
   at least one essential oil,
   at least one of lactic acid ethyl ester and lactic acid n-butyl ester, and
   at least one sprout inhibitor.

8. The tuber according to claim 7, wherein the tuber is a potato tuber.

9. A method, comprising applying the composition of claim 1 onto the surface of a tuber.

10. The method according to claim 9, wherein the tuber is a potato tuber.

11. The method according to claim 10, wherein the potato tuber is sprayed with the composition of claim 1, in neat form or diluted with water, on the line.

12. The method of claim 11 wherein the potato tuber is from a cultivar selected from the group consisting of Russet Burbank, Ranger Russet, Umatilla Russet, Shepody, Norkotah Russet, Yukon Gold, Norchip, Gem Russet, Atlantic, Chipeta, Snowden, and Dark Red Norland.

13. The composition according to claim 1, comprising at least one essential oil that comprises eugenol.

14. The tuber according to claim 8, wherein the potato tuber is from a cultivar selected from the group consisting of Russet Burbank, Ranger Russet, Umatilla Russet, Shepody, Norkotah Russet, Yukon Gold, Norchip, Gem Russet, Atlantic, Chipeta, Snowden, and Dark Red Norland.

15. The tuber according to claim 7, comprising clove oil on at least a part of a surface thereof.

16. The composition according to claim 1, comprising at least one sprout inhibitor selected from the group consisting of chloroisopropyl-N-carbamate (CIPC), maleic hydrazide (MH), dimethylnaphthalene (DMN) and diisopropylnaphthalene (DIPN).

17. The composition according to claim 1, comprising chloroisopropyl-N-carbamate (CIPC).

18. The tuber according to claim 7, comprising on at least at least a part of a surface thereof at least one sprout inhibitor selected from the group consisting of chloroisopropyl-N-carbamate (CIPC), maleic hydrazide (MH), dimethylnaphthalene (DMN) and diisopropylnaphthalene (DIPN).

19. The tuber according to claim 7, comprising on at least at least a part of a surface thereof chloroisopropyl-N-carbamate (CIPC).

20. The tuber according to claim 8, comprising on at least at least a part of a surface thereof chloroisopropyl-N-carbamate (CIPC).

* * * * *